United States Patent [19]

Sandler

[11] Patent Number: 4,748,702
[45] Date of Patent: Jun. 7, 1988

[54] PILLOW DESIGNED TO REDUCE SNORING BY A USER THEREOF

[75] Inventor: Peter H. Sandler, Willowdale, Canada

[73] Assignee: Thera-P-Cushion Products, Toronto, Canada

[21] Appl. No.: 38,635

[22] Filed: Apr. 14, 1987

[51] Int. Cl.⁴ .............................................. A47G 9/00
[52] U.S. Cl. ........................................ 5/434; 5/436; 128/135
[58] Field of Search ............... 5/434, 436, 440, 437; 128/135

[56] References Cited

U.S. PATENT DOCUMENTS

| | | |
|---|---|---|
| 655,087 | 7/1900 | Jones . |
| 1,020,444 | 3/1912 | Platt . |
| 1,194,200 | 8/1916 | Lowder . |
| 2,522,120 | 9/1950 | Kaskey . |
| 2,880,428 | 4/1959 | Forsland . |
| 2,940,088 | 6/1960 | Boos .................................... 5/436 |
| 3,000,670 | 9/1961 | Clark . |
| 3,070,402 | 12/1962 | Stanton . |
| 3,239,854 | 3/1966 | Freedlander . |
| 3,403,414 | 10/1968 | Unger . |
| 3,521,310 | 7/1970 | Greenwalt . |
| 3,667,074 | 6/1972 | Emery . |
| 3,757,364 | 9/1973 | Downing . |
| 3,757,365 | 9/1973 | Kretchmer . |
| 3,842,453 | 10/1974 | Redfield ................................. 5/434 |
| 4,118,813 | 10/1978 | Armstrong . |
| 4,218,792 | 8/1980 | Kogan .................................. 5/436 |
| 4,349,925 | 9/1982 | Macomber . |
| 4,536,905 | 8/1985 | De Santis ............................. 5/436 |

FOREIGN PATENT DOCUMENTS

| | | |
|---|---|---|
| 136170 | 4/1947 | Australia . |
| 753552 | 2/1967 | Canada . |
| 2263740 | 10/1975 | France ................................. 5/436 |
| 2305956 | 10/1976 | France ................................. 5/434 |

Primary Examiner—Alexander Grosz
Attorney, Agent, or Firm—Merchant, Gould, Smith, Edell, Welter & Schmidt

[57] ABSTRACT

A pillow has two intersecting channels formed in its upper face. One channel accommodates the user's head, the other the user's neck. A relatively hard object is located in or under the first channel and also adjacent the second channel. The relatively hard object functions so as to make it uncomfortable for a user to rest the back of the user's head on the hard object, while not being relatively uncomfortable if the user moves his/her head to one side or the other. The pillow is designed so that when the user's head is on one side or the other thereof, a part of the pillow engages the user's lower jaw, causing the user's mouth to be closed.

8 Claims, 4 Drawing Sheets

PILLOW DESIGNED TO REDUCE SNORING BY A USER THEREOF

BACKGROUND OF THE INVENTION

This invention relates to pillows designed so as to inhibit snoring by persons using the pillows or, at least, to reduce the tendency of a person using such a pillow to snore, as compared with the tendency of such a person to snore using a conventional pillow.

In order to reduce the tendency of a person to snore, it is necessary to ensure that the person's head lies on one side or the other, i.e., that the person is not lying with the back of the person's head on the pillow, and that the person's mouth is kept closed. Snoring most commonly occurs when a person is lying on his/her back with the back of his/her head on a pillow, the result of which commonly is opening of the person's mouth and air being drawn in through the person's mouth. The rush of this air through the person's air passages causes vibration of loose tissue in the person's air passages, and the noise of this vibration is what is known as snoring.

A so-called anti-snore pillow is disclosed in U.S. Pat. No. 4,536,905, issued Aug. 27, 1985, Damian G. De Santis. That patent discloses the incorporation into a pillow of a semi-soft brace, which causes discomfort to the head of a person using the pillow if that person's head is in the dorsal position. The brace tends to force the user's head to one side or the other, but the shape of the brace, as well as a downward inclination of the upper surface of the pillow from back to front thereof, also tends to force the user's head inwardly towards the user's chest. This is an uncomfortable position to maintain for an extended period of time and could give rise to a sore neck. Furthermore, a person whose head is in this position has his/her air passage restricted at some point, as compared to the air passage of a person whose head is erect, i.e., in the position of a person's head relative to that person's trunk when walking. A restriction in a person's air passage causes an increase in the velocity of the air passing through the restricted portion and may result in a greater degree of snoring than otherwise if the person should breathe through his/her mouth.

So-called cervical pillows are known for providing support for the head and neck of a user. Such pillows sometimes include a central channel for receiving the head of a user, raised front and rear portions, and another channel of lesser depth than the first in the raised front portion for providing support for the neck of the user. No claims are made for pillows of this type having any effect as far as snoring is concerned. The design of such pillows is dictated solely by the criteria of comfort, support and proper posture.

SUMMARY OF THE INVENTION

In accordance with this invention there is provided a pillow which is designed to reduce the tendency of a person using it to snore, as compared with that person's tendency to snore when using a conventional pillow.

In accordance with one aspect of this invention there is provided a pillow comprising a body of resilient, compressible material having a front edge, a rear edge, two side edges, a bottom face and an upper face, said upper face having a first channel formed therein for receiving the head of a user, said first channel extending substantially parallel to said front edge and for a length greater than the depth of the head of a user, a portion of said pillow between said front edge and said first channel being raised above the level of the bottom of said first channel and having a second channel formed therein extending between said front edge and said first channel, the level of the bottom of said second channel relative to said bottom face being higher than the level of the bottom of said first channel relative to said bottom face, said second channel being adapted to receive the neck of a user, and a relatively hard object located in or under said first channel at a location adjacent said second channel, said relatively hard object being shaped and located so as to make it uncomfortable for a user to rest the user's head on the pillow with the back of the user's head in said first channel and over said relatively hard object but comfortable if the user's head is moved onto one side of the user's face or the other, the parts of said portion of said pillow adjacent the intersection of said first and second channels constituting means for engaging the lower jaw of a user when the user's face is on one side thereof or the other to hold the mouth of the user shut.

BRIEF DESCRIPTION OF THE DRAWINGS

This invention will become more apparent from the following detailed description, taken in conjunction with the appended drawings, in which.

DETAILED DESCRIPTION OF THE INVENTION INCLUDING THE PREFERRED EMBODIMENT

Figure 1:
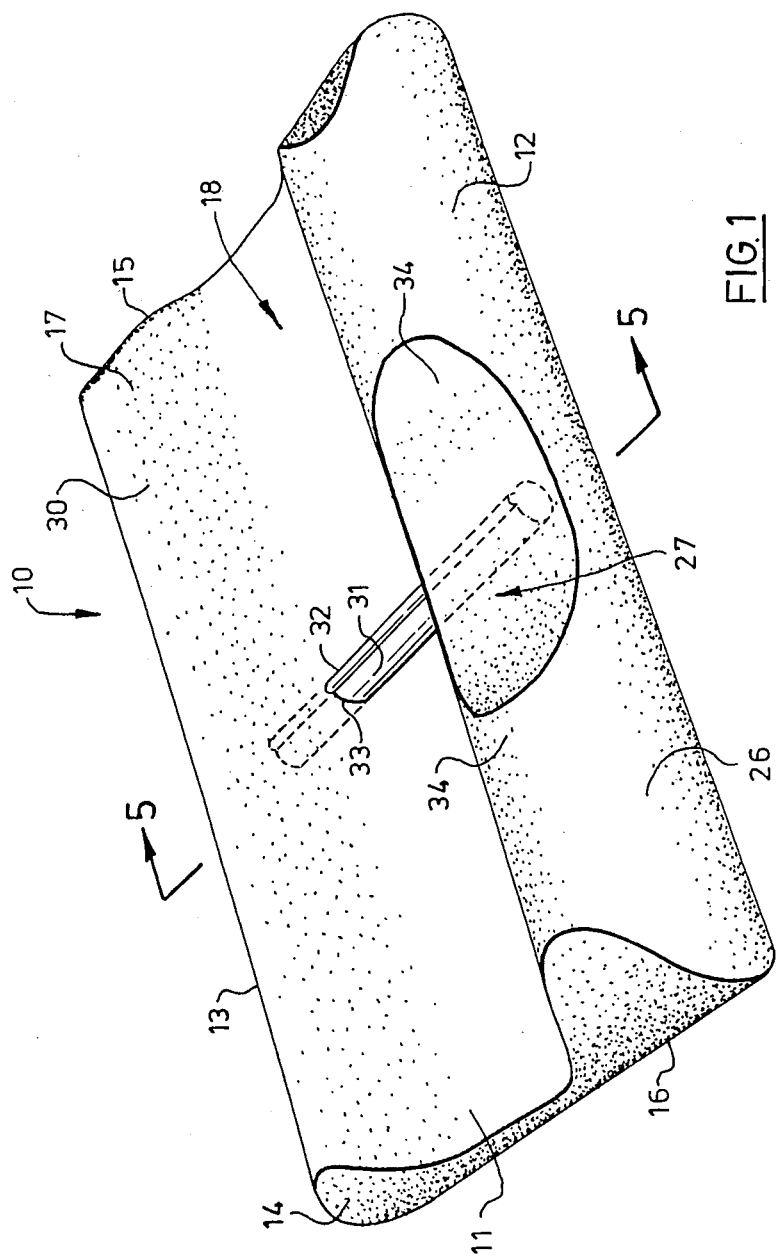
FIG. 1 is a perspective view of a pillow embodying the present invention.

A pillow embodying the present invention may assume a number of different basic shapes. However, in its preferred embodiment the pillow is as shown in the Figures. Thus, referring to FIGS. 1-5, a pillow 10 embodying the present invention includes a body 11 of resilient, compressible material. This material may be foam rubber, for example, or one of the foamed plastic materials that have largely replaced foam rubber. Foamed polyurethane is particularly preferred.

Pillow 10 has a front edge 12, a rear edge 13, two side edges 14 and 15, a bottom face 16 and an upper face 17. Front, rear and side edges 12-15 preferably are smoothly curved, as shown, with the front and rear edges being parallel to each other and the side edges also being parallel to each other. In plan pillow 10 is essentially rectangular.

Bottom face 16 is essentially flat. Upper face 17, however, has a channel 18 formed therein for receiving the head 19 (FIGS. 2-4) of a user. Channel 18 extends substantially parallel to front edge 12 and, in the embodiment illustrated, extends between side edges 14 and 15. It would be sufficient, however, if channel 18 were to terminate short of either or both side edges 14 and 15 as long as it extended for a length greater than the depth (from nose to back of the head) of the head 19 of the user. Channel 18 basically has a flat or slightly downwardly curved bottom 21 (FIG. 5) joined via smoothly curved sections 22 and 23 to an upwardly and rearwardly inclined wall 24 and an upwardly and forwardly inclined wall 25, all as best seen in FIG. 5.

A portion 26 of pillow 10 between front edge 12 and channel 18 is raised above the level of bottom 21 of channel 18 and has a second channel 27 (FIGS. 1 and 5) formed therein extending between front edge 12 and channel 18.

Figure 5:
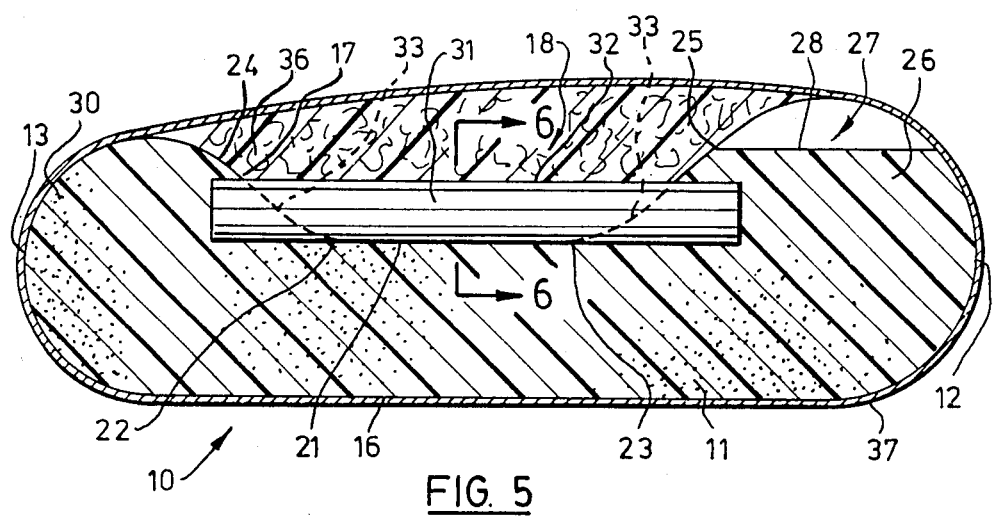
FIG. 5 is a section taken along line 5—5 in FIG. 1.
Figure 6:
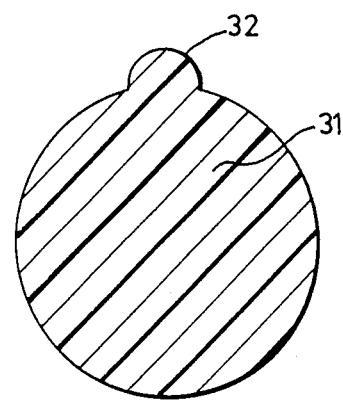
FIG. 6 is a section taken along line 6—6 in FIG. 5.

As best shown in FIG. 5, the level of the bottom 28 of channel 27 is higher relative to bottom face 16 than the level of bottom 21 of channel 18. Channel 27 is adapted to receive the neck of a user and, to that end, preferably is smoothly curved in a configuration like that of the outer surface of the neck of a user.

A portion 30 of pillow 10 between rear edge 13 and channel 18 also is raised above the level of bottom 21 of channel 19 and is similar in appearance to portion 26 but slightly smaller than portion 26. Thus, portion 30 may have a radius of curvature of about 2¼", while portion 26 may have a radius of curvature of about 2½". The depth of the pillow measured between front and rear edges 12 and 13 may be about 17", while the length of the pillow may be about 24".

Located in channel 18 is a relatively hard object 31. In the illustrated embodiment object 31 is a cylinder of rubber about 1" in diameter and about 8" long having a rib 32 formed integral therewith on the upper surface of the cylinder. Cylindrical object 31 is removably located in channel 18 by having its two ends inserted in openings 33 formed in walls 24 and 25. Object 31 alternatively could be located below bottom 21 of channel 18. Object 31 also is located adjacent to channel 27. Indeed, preferably it lies with its longitudinal axis in registry with the longitudinal axis of channel 27.

Figure 2:
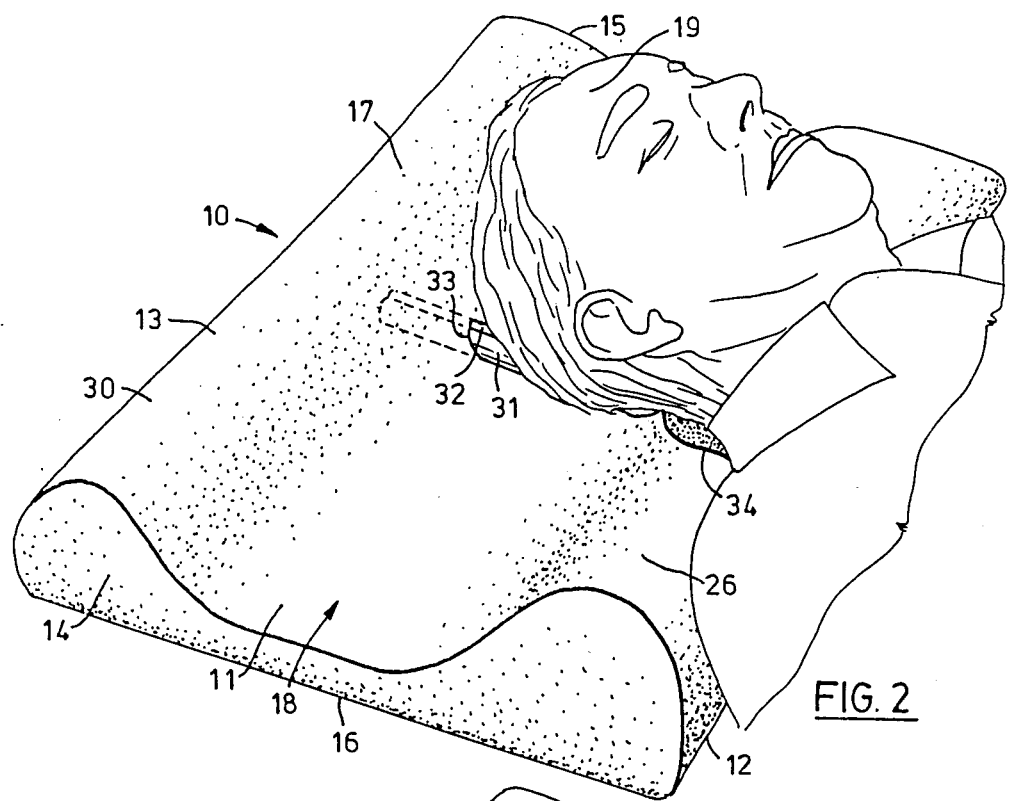
FIGS. 2 and 3 illustrate a pillow embodying this invention in use.
Figure 3:
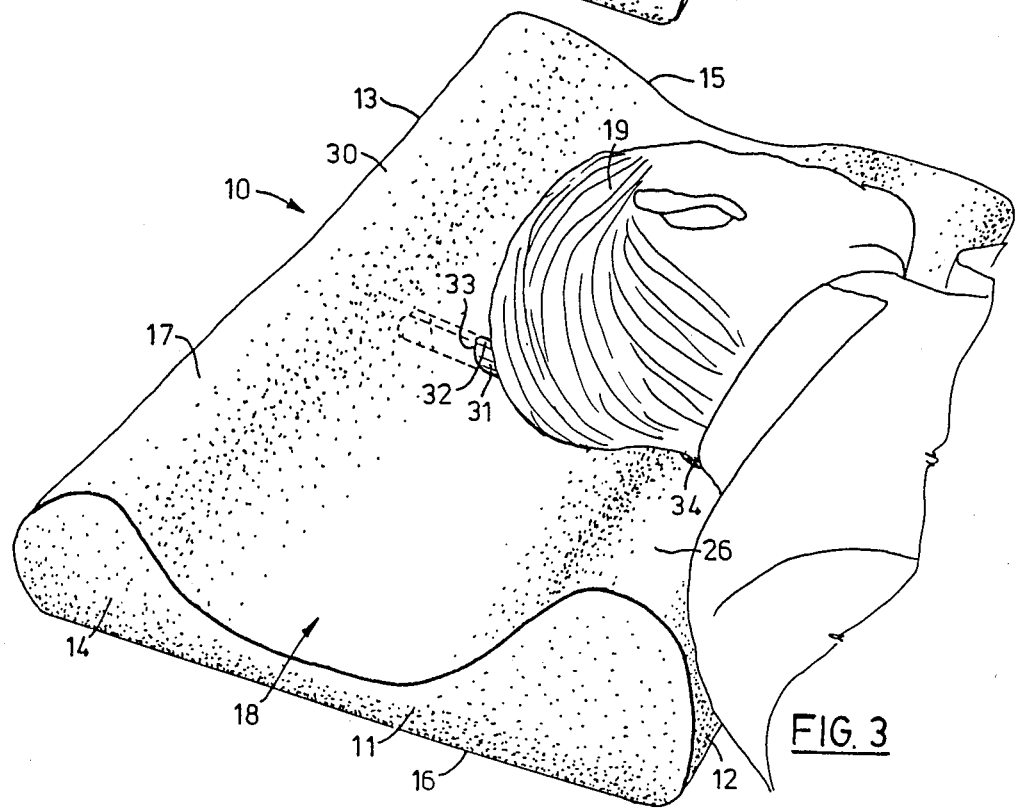

Object 31 functions so as to make it uncomfortable for a user to rest his/her head on pillow 10 with the back of the user's head in channel 18 and on object 31, i.e., the position shown in FIG. 2. On the other hand, object 31 does not present any substantial amount of discomfort to a user's head turned to one side or the other, as shown in FIGS. 3 and 4, so object 31 essentially forces a user to sleep on one side or the other of his/her head rather than on the back thereof.

Figure 4:
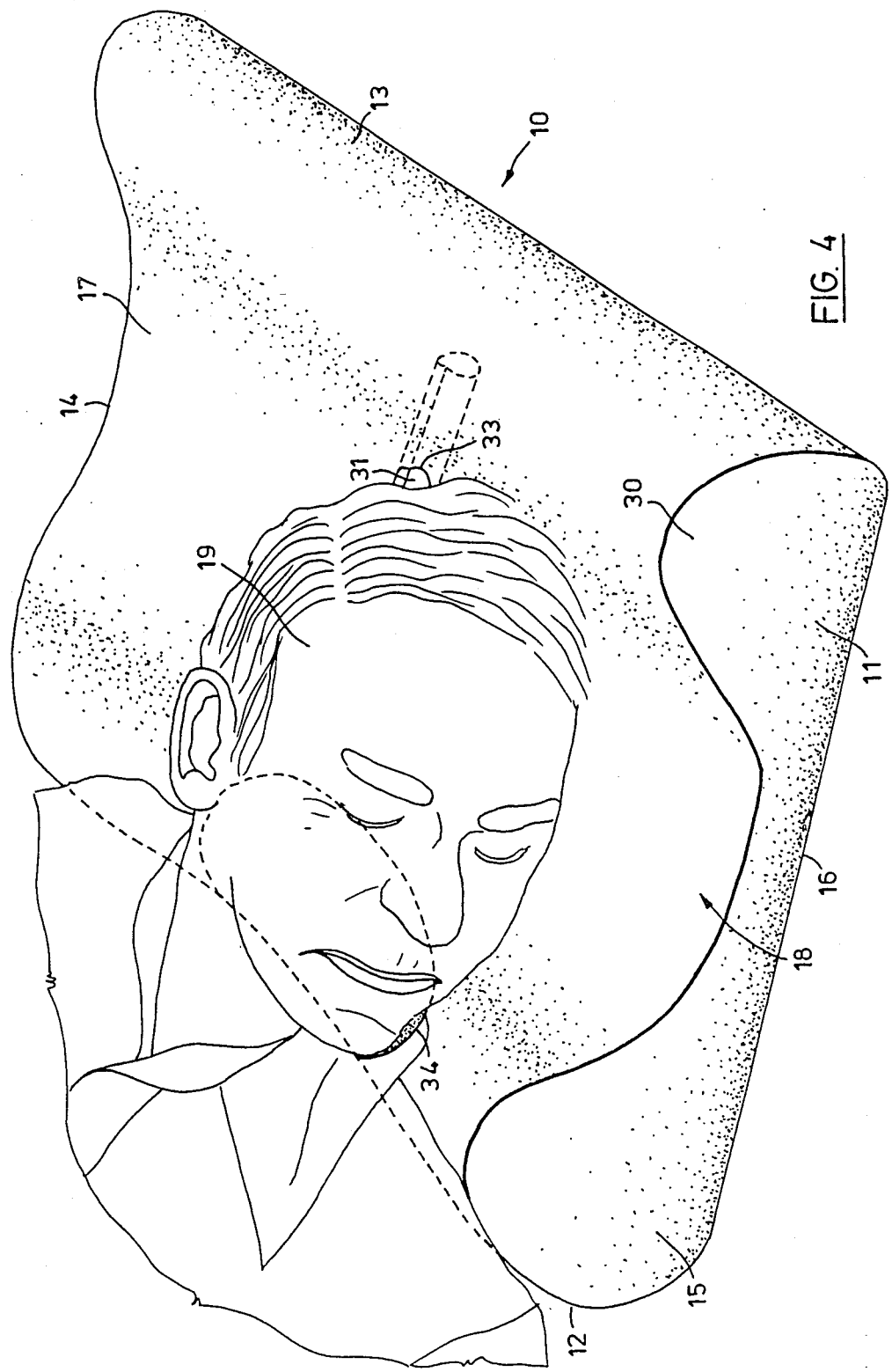
FIG. 4 is a view similar to FIG. 3 but from the side of the pillow towards which the face of the user is directed.

The parts 34 of portion 26 of pillow 10 adjacent the intersection of channels 18 and 27 physically engage the lower jaw of a user when the user's face is on one side thereof or the other to hold the mouth of the user shut, as best shown in FIG. 4.

If pillow 10 is not not to be used as an anti-snore pillow, but solely as a pillow with cervical support, object 31 should be removed and the pillow turned so that the front edge becomes the back edge and vice versa. When so used, channel 27 has no function and the neck of the user is supported by portion 30.

It is desirable in either case to employ a batt 36 (FIG. 5) of suitable fibres in channel 18. This batt of fibres can be shaped by the user to provide maximum comfort. Dacron ® is a suitable material for the fibres.

Both pillow 10 and batt 36 may be encased in a removable pillow-case 37, as shown in FIG. 5.

By virtue of usage of a pillow embodying the present invention, the head of the user is directed to one side, the user's mouth is kept shut by engagement of a part of the pillow with the user's lower jaw, and the user's head is kept in its normal erect position with respect to the trunk of the user's body with the user's air passages unrestricted.

The embodiments of the invention in which an exclusive property or privilege is claimed are defined as follows:

1. A pillow comprising a body of resilient, compressible material having a front edge, a rear edge, two side edges, a bottom face and an upper face, said upper face having a first channel formed therein for receiving the head of a user, said first channel extending substantially parallel to said front edge and for a length greater than the depth of the head of a user, a portion of said pillow between said front edge and said first channel being raised above the level of the bottom of said first channel and having a second channel formed therein extending between said front edge and said first channel, the level of the bottom of said second channel relative to said bottom face being higher than the level of the bottom of said first channel relative to said bottom face, said second channel being adapted to receive the neck of a user, and a relatively hard object located in or under said first channel at a location adjacent said second channel, said relatively hard object being shaped and located so as to make it uncomfortable for a user to rest the user's head on the pillow with the back of the user's head in said first channel and over said relatively hard object but comfortable if the user's head is moved onto one side of the user's face or the other, the parts of said portion of said pillow adjacent the intersection of said first and second channels constituting means for engaging the lower jaw of a user when the user's face is on one side thereof or the other to hold the mouth of the user shut.

2. A pillow according to claim 1 wherein said relatively hard object is fabricated of rubber.

3. A pillow according to claim 1 wherein said relatively hard object has its longitudinal axis extending substantially parallel to the longitudinal axis of said second channel.

4. A pillow according to claim 1 wherein said relatively hard object has a rib on its upper surface.

5. A pillow according to claim 1 wherein said first channel has a relatively flat bottom, an upwardly and rearwardly inclined rear wall and an upwardly and forwardly inclined front wall.

6. A pillow according to claim 1 wherein said second channel is curved to approximate the contour of the neck of a user.

7. A pillow comprising a body of resilient, compressible material having a front edge, a rear edge, two side edges, a bottom face and an upper face, said upper face having a first channel formed therein for receiving the head of a user, said first channel extending substantially parallel to said front edge and for a length greater than the depth of the head of a user, a portion of said pillow between said front edge and said first channel being raised above the level of the bottom of said first channel and having a second channel formed therein extending between said front edge and said first channel, the level of the bottom of said second channel relative to said bottom face being higher than the level of the bottom of said first channel relative to said bottom face, said second channel being adapted to receive the neck of a user, and a relatively hard object of cylindrical configuration and having a rib at its upper end located in or under said first channel at a location adjacent said second channel, said relatively hard object being shaped and located so as to make it uncomfortable for a user to rest the user's head on the pillow with the back of the user's head in said first channel and over said relatively hard object but comfortable if the user's head is moved onto one side of the user's face or the other, the parts of said portion of said pillow adjacent the intersection of said first and second channels constituting means for engaging the lower jaw of a user when the user's face is on one side thereof or the other to hold the mouth of the user shut.

8. A pillow comprising a body of resilient, compressible material having a front edge, a rear edge, two side edges, a bottom face and an upper face, said upper face having a first channel formed therein for receiving the head of a user, said first channel extending substantially parallel to said front edge and for a length greater than the depth of the head of a user, a portion of said pillow between said front edge and said first channel being raised above the level of the bottom of said first channel and having a second channel formed therein extending between said front edge and said first channel, the level of the bottom of said second channel relative to said bottom face being higher than the level of the bottom of said first channel relative to said bottom face, said second channel being adapted to receive the neck of a user, and a relatively hard object removably located in or adjacent to said first channel at a location adjacent said second channel, said relatively hard object being shaped and located so as to make it uncomfortable for a user to rest the user's head on the pillow with the back of the user's head in said first channel and over said relatively hard object but comfortable if the user's head is moved onto one side of the user's face or the other, the parts of said portion of said pillow adjacent the intersection of said first and second channels constituting means for engaging the lower jaw of a user when the user's face is on one side thereof or the other to hold the mouth of the user shut.

* * * * *